United States Patent [19]

Kim

[11] Patent Number: 4,883,869
[45] Date of Patent: Nov. 28, 1989

[54] NOVEL BETA-LACTAMS CONTAINING AMINO ACID SUBSTITUENTS

[75] Inventor: Kyoung S. Kim, Portage, Mich.

[73] Assignee: The Upjohn Company, Kalamazoo, Mich.

[21] Appl. No.: 249,242

[22] Filed: Sep. 22, 1988

Related U.S. Application Data

[63] Continuation of Ser. No. 85,912, Aug. 14, 1987, abandoned, which is a continuation-in-part of Ser. No. 789,158, Oct. 24, 1985, abandoned, which is a continuation-in-part of Ser. No. 683,975, Dec. 20, 1984, abandoned.

[51] Int. Cl.$^4$ .................. C07D 205/08; C07D 417/14; C07D 417/12; A61K 31/425
[52] U.S. Cl. .................................................. 540/355
[58] Field of Search ......................................... 540/355

[56] References Cited

U.S. PATENT DOCUMENTS 4,478,749 10/1984 Koster et al. ................... 260/245.4

FOREIGN PATENT DOCUMENTS 2748258 10/1977 European Pat. Off.
053815 6/1982 European Pat. Off.
053816 6/1982 European Pat. Off.
053387 8/1982 European Pat. Off.
061765 10/1982 European Pat. Off.
091239 3/1983 European Pat. Off.
076758 4/1983 European Pat. Off.
093376 4/1983 European Pat. Off.
096297 5/1983 European Pat. Off.
111326 12/1983 European Pat. Off.

OTHER PUBLICATIONS

Chambers et al., Chem. Abs. 106, 18244 (7-16-86).

*Primary Examiner*—Mark L. Berch
*Attorney, Agent, or Firm*—Paul W. Busse; Donald L. Corneglio

[57] ABSTRACT

An antimicrobially active compound of the formula

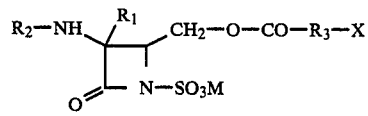

and pharmaceutically acceptable salts thereof: wherein $R_1$ is hydrogen, —OCH$_3$, or —NH—CHO; $R_2$ is an acyl group derived from a carboxylic acid; $R_3$ is selected from the group consisting of —CH$_2$—, —CH$_2$CH$_2$—, —CH$_2$CH$_2$CH$_2$—, and —CH$_2$CH$_2$CH$_2$CH$_2$— and when X is NL$_2$L$_3$ then —CH$_2$CH$_2$—, —CH$_2$CH$_2$CH$_2$—, and —CH$_2$CH$_2$CH$_2$CH$_2$— are optionally substituted with one substituent selected from the group consisting of (C$_1$-C$_4$)alkyl, (C$_1$-C$_4$)carboxyalkyl, or (C$_1$-C$_4$)alkylthio; X is —NL$_2$L$_3$ or a pyrrole of the formula

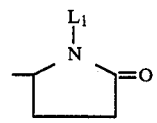

wherein L$_1$ is hydrogen, —CO—O—CH$_2$—(C$_6$H$_5$), or SO$_3$H; L$_2$ is hydrogen, or SO$_3$H; and L$_3$ is hydrogen, —CO—(C$_1$-C$_4$)alkyl; —CH=NH, —C(NH$_2$)=NH, —CO—O—CH$_2$—(C$_6$H$_5$), —COH, or —SO$_3$H with the proviso that if one of L$_2$ or L$_3$ is —SO$_3$ then the other is hydrogen.

7 Claims, No Drawings

NOVEL BETA-LACTAMS CONTAINING AMINO ACID SUBSTITUENTS

CROSS REFERENCE TO RELATED APPLICATIONS

This application is a continuation of U.S. Ser. No. 085,912, filed Aug. 14, 1987, abandoned, which was a continuation-in-part of U.S. Ser. No. 789,158, filed Oct. 24, 1985, abandoned, which was a continuation-in-part of U.S. Ser. No. 683,975 filed Dec. 20, 1984, abandoned.

FIELD OF THE INVENTION

This invention encompasses novel 2-azetidinone sulfonic acid compounds which have useful antimicrobial activity.

INFORMATION DISCLOSURE

The following documents may be material to the examination of this application.

EP 0 053 816 discloses azetidinone sulfonic acids substituted on the β-lactam ring at position $C_4$. Although this document claims any organic residue as a $C_4$ substituent, this document does not teach the specific $C_4$ substituents claimed in this case.

EP 053 815, EP 076 758, EP 096 297, EP 093 376 all disclose azetidinone sulfonic acids substituted on the β-lactam ring. The substituents on the β-lactam ring at position $C_4$ taught by these documents are different than the $C_4$ substituents claimed in this case.

U.S. Pat. No. 4,478,749 and EP 061 765 disclose azetidinones substituted on the β-lactam ring. These documents teach phosphine derivatives on the lactam ring nitrogen atom and do not teach the sulfonic acid derivatives claimed in this invention.

EP 111 326 discloses a process to prepare chiral azetidinone sulfonic acids. This document teaches only one substituent on the $C_4$ carbon atom. This substituent is not claimed in this case.

EP 091 236 discloses silylated azetidinones as intermediates to β-lactams. The silylated intermediates taught by this document are not claimed in this case.

EP 27 48 258 discloses azetidinones substituted on the β-lactam ring. The document does not teach the azetidinone sulfonic acid derivatives claimed in this case.

EP 053 387 discloses azetidinones derivatives. This document does not teach any substitution on the lactam ring at $C_4$.

SUMMARY OF THE INVENTION

The present invention teaches novel 2-azetidinone sulfonic acid derivatives containing amino acid substituents which are useful as microbial growth inhibitors. This invention includes enantiomers, diastereomeric and racemic mixtures of these compounds. Intermediates and processes for preparing these compounds are also disclosed.

Novel 2-azetidinone compounds within the scope of this invention are represented by Formula I and pharmaceutically acceptable salts thereof wherein $R_1$ is hydrogen, $-OCH_3$, or $-NH-CHO$, wherein $R_2$ is an acyl group derived from a carboxylic acid; wherein $R_3$ is selected from the group consisting of $-CH_2-$, $-CH_2CH_2-$, $-CH_2CH_2CH_2-$, and $-CH_2CH_2CH_2CH_2-$ wherein X is $NL_2L_3$ then $-CH_2CH_2-$, $-CH_2CH_2CH_2-$ and $-CH_2CH_2CH_2CH_2-$ are optionally substituted with 1 substituent selected from the group consisting of $(C_1-C_4)$alkyl, $(C_1-C_4)$alkoxy, $(C_1-C_4)$alkylthis, and $(C_1-C_4)$carboxyalkyl; wherein X is $-NL_2L_3$ or a pyrrole of Formula II; wherein $L_1$ is hydrogen, $(C_1-C_4)$alkyl, $-(C_6H_5)$, $-COH$, $-CO-O-CH_2-(C_6H_5)$ or $SO_3M$; wherein $L_2$ and $L_3$ are the same or different and are hydrogen, $(C_1-C_4)$alkyl, $-CO-(C_1-C_4)$alkyl, $(C_1-C_4)$carboxyalkyl, $=CH=NH$, $-C(NH_2)=NH$, $-(C_6H_5)$, $-CO-O-CH_2-(C_6H_5)$, $-COH$, or $-SO_3M$ with the proviso that if one of $L_2$ or $L_3$ is $-SO_3M$, the other is hydrogen and wherein M is hydrogen, sodium, potassium or a quaternary ammonium salt.

Novel compounds within the scope of this invention which are useful as intermediates to 2-azetidinone sulfonic acid derivatives having microbial growth inhibition include compounds of Formula I wherein $L_1$ or $L_2$ are $-CO-O-CH_2-(C_6H_5)$.

A detailed description of the acyl groups included in $R_2$ is found in U.S. Pat. No. 4,478,749, column 8, line 41 to column 12, line 50, as those terms are defined at column 7, line 34 through column 8. line 22, all of which is incorporated by reference herein.

Preferred acyl groups of $R_2$ include those which have been used to acylate 6-aminopenicillanic acid, 7-aminocephalosporic acid and their derivatives which can be found in "Chemistry and Biology of β-Lactam Antibiotics, Vol. 1, R. B. Morin and M. Gorham, ed., Academic Press, N.Y.1982 and include the following fragments: 2-Cyanoacetyl, Aminophenylacetyl, Amino(4-hydroxyphenyl)acetyl, α(Thien-2-yl)acetyl, α(-Thien-3-yl)acetyl, Phenylacetyl, Hydroxyphenylacetyl, (Formyloxy)-phenylacetyl, [(Trifluoromethyl)thio]acetyl, 2-(3,5-Dichloro-4-oxo-1-(4H)-pyridyl)acetyl, (1H-Tetrazol-1-yl)acetyl, (2-Amino-4-thiazolyl)-2-methoxyiminoacetyl, 2-[(Cyanomethyl)thio]acetyl, [[(4-Ethyl-2,3-dioxo-1-piperizinyl)carbonyl]amino]phenylacetyl, [[(4-Ethyl-2,3-di-oxo-piperazinyl)carbonyl]amino](4-hydroxyphenyl)acetyl, 2-(Aminomethyl)-phenylacetyl, 4-(Carbamoylcarboxymethylene)-1,3-dithiethane-2-carbonyl, 3-(o-Chlorophenyl)-5-methyl-4-isoxazolecarbonyl, 2-p-[(1-4,5,6-Tetrahydro-2-pyrimidinyl)phenyl]acetyl, Amino-1,4-cyclohexadien-1-yl-acetyl, Phenylsulfoacetyl, (2R)-2-amino-2-(m-methanesulfonamidophenyl)acetyl, (2-Amino-4-thiazolyl)-2-(1-carboxy-1-methylethoxy)iminoacetyl, 2-(1H-Tetrazol-1-yl)acetyl, (2,3-Dihydro-2-imino-4-thiazolyl)(methoxyimino)acetyl, (2-Amino-4-thiazol)-carboxymethoxyiminoacetyl, (2-Aminopyridin-6-yl)methoxyiminoacetyl, (2-Aminopyridin-6-yl)carboxymethoxyiminoacetyl, (4-Amino-2-pyrimidyl)methoxyiminoacetyl, (5-Amino-1,2,4-thiadiazol-3-yl)-2-methoxyiminoacetyl, (5-Amino 1,2,4-thiadiazol 3-yl)-2-carboxymethoxyiminoacetyl, (5-Amino-1,2,4-thiadiazol-3-yl) 1-carboxy-1-methylethoxy)iminoacetyl, D-α[[(Imidazolidin-2-on-1-yl)-carbonyl]amino]-phenylacetyl, D-α[[(3-mesyl-imidazolidin-2-on-1-yl)carbonyl]amino]phenylacetyl, 2,6-Dimethylbenzoyl, (S)-2-(4-hydroxy-1,5-naphthyridine-3-carboxamido-2-phenylacetyl.

Preferred compounds within the scope of this invention include compounds wherein the organic acid derivative, $R_2$, is an oximinoacyl moiety represented by Formula III wherein $R_4$ is $-CH_3$, $-CH_2-CO_2-R_5$, or $-C(CH_3)_2-CO_2-R_5$; wherein $R_5$ is hydrogen, $(C_1-C_4)$ alkyl, $-CH(C_6H_5)_2$, $-CH_2(C_6H_5)$, or a cation; and wherein $R_6$ is hydrogen, $-CO-O-C(CH_3)_3$, $-CO-O-CH_2-(C_6H_5)$, or $-C(C_6H_5)_3$.

Novel compounds within the scope of this invention wherein $R_2$ is an oximinoacyl moiety represented by Formula III which are useful as intermediates to 2-azetidinone sulfonic acid derivatives having microbial growth inhibition include compounds wherein $R_5$ is $(C_1-C_4)$ alkyl, $-CH(C_6H_5)_2$, or $-CH_2(C_6H_5)$; and wherein $R_6$ is $-CO-O-C(CH_3)_3$, $-CO-O-CH_2-(C_6H_5)$, or $-C(C_6H_5)_3$.

DETAILED DESCRIPTION

The compounds of this invention are identified in two ways: by a descriptive chemical name and by numerical identification which corresponds to the appropriate structure contained in the structure charts. In appropriate situations, the proper stereochemistry is represented in the structure charts as well.

The various carbon moieties are defined as follows: Alkyl refers to an aliphatic hydrocarbon radical and includes branched or unbranched forms such as methyl, ethyl, n-propyl, isopropyl, n-butyl, isobutyl, sec-butyl, t-butyl.

Alkoxy refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, and t-butoxy.

Alkylthio refers to an alkyl radical which is attached to the remainder of the molecule by sulfur and includes branched or unbranched forms such as methylthio, ethylthio, n-propylthio, isopropylthio, n-butylthio, isobutylthio, sec-butylthio, and t-butylthio.

Carboxyalkyl refers to an alkoxy radical which is attached to the remainder of the molecule by a carbonyl group and includes branched or unbranched forms such as methoxycarbonyl, ethoxycarbonyl, propoxycarbonyl, isopropoxycarbonyl, butoxycarbonyl, isobutoxycarbonyl, sec-butoxycarbonyl, and t-butoxycarbonyl.

Unless otherwise indicated, in the above description and throughout this document the parenthetical term $(C_n-C_m)$ is inclusive such that a compound of $(C_1-C_4)$ would include compounds of 1, 2, 3 and 4 carbons and their isomeric forms.

It will be apparent to those skilled in the art that compounds of this invention may exist in different tautomeric forms. The scope of this invention includes all tautomeric forms in addition to those represented in the formulas used herein.

It will be apparent to those skilled in the art that compounds of this invention may contain several chiral centers. The scope of this invention includes all enantiomeric or diastereomeric forms of Formula I compounds either in pure form or as mixtures of enantiomers or diastereomers. Specifically, the azetidinones of this invention have chiral carbon atoms at positions $C_3$ and $C_4$ of the $\beta$-lactam ring. The preferred form is cis at centers 3 and 4 and the preferred stereochemistry at $C_3$ and $C_4$ is 3(S) and 4(S). The phrase "cis at centers 3 and 4" means that the substituents at C-3 and C-4 are both oriented on the same side of the $\beta$-lactam ring.

The scope of this invention includes the pharmaceutically acceptable acid salts of the disclosed compounds. Acid salts are formed by reacting the compounds described herein with the appropriate acid in a suitable solvent. Suitable acids for this purpose include hydrochloric, sulfuric, phosphoric, hydrobromic, hydroiodic, acetic, lactic, citric, succinic, benzoic, salicylic, palmoic, cyclohexansulfamic, methanesulfonic, naphthalenesulfonic, p-toluenesulfonic, maleic, fumaric, or oxalic.

The scope of this invention includes the pharmaceutically acceptable salts of the disclosed compounds. Such salts include the following cations but are not limited to these: alkali metal ions such as potassium, sodium, lithium, alkaline earth metal ions such as magnesium or calcium and ammonium ions such as ammonium, tetralkylammonium and pyridinium Metal salts are formed by suspending the compounds in water or other suitable solvent and adding a dilute metal base such as sodium or potassium bicarbonate until the pH is between 6 and 7.

The compounds of this invention and their respective pharmaceutically acceptable salts have antibiotic activity against a variety of gram-negative bacteria including *Escherichia coli, Klebsiella pneumoniae,* and *Pseudomonas aeruginosa.* The compounds are useful for treating bacterial infections in animals, including and most preferably humans. Compounds of the invention are tested for in vitro antimicrobial activity using standard testing procedures such as the determination of minimum inhibitory concentration (MIC) by methods described in "Methods for Dilution Antimicrobial Susceptibility Tests for Bacteria That Grow Aerobically" (M7-A) Published December 1985 by the National Committee for Clinical Laboratory Standards, 771 East Lancaster Avenue, Villanova, PA 19084. Briefly, MIC values are determined in unsupplemented Mueller Hinton Agar (MHA). The compounds tested are diluted serially into molten MHA at 47° C. The agar is poured into petri dishes and allowed to harden. The various bacteria used for testing are grown overnight on MHA at 35° C. and transferred to Tryptiease Soy Broth (TSB) until a turbidity of 0.5 McFarland standard is obtained. The bacteria are diluted one to twenty in TSB and inoculated on the plates (1 $\mu$l using a Steers replicator). The plates are incubated at 35° C. for 20 hours and the MIC is read to be the lowest concentration of drug that completely inhibits visible growth of the bacterium. The MIC test results of two typical compounds of this invention are given in Table I.

Various compositions of the present invention are presented for administration to humans and animals in unit dosage forms, such as tablets. capsules, pills, powders, granules, sterile parenteral solutions or suspensions, eye drops, solutions or suspensions, and emulsions containing suitable quantities of compounds of Formula I.

For oral administration solid or fluid unit dosage forms can be prepared. For preparing solid compositions, the compounds of this invention are mixed with conventional ingredients such as talc, magnesium stearate, dicalcium phosphate, magnesium aluminum silicate, calcium sulfate, starch, lactose, acacia, methylcellulose, and/or functionally similar pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

For preparing fluid compositions, the compounds of this invention are dissolved in an aqueous vehicle together with sugar, aromatic flavoring agents and preservatives to form a syrup. An elixir is prepared by using a hydroalcoholic vehicle such as ethanol, suitable sweeteners such as sugar and saccharin, and aromatic flavoring agents. Suspensions are prepared in an aqueous vehicle with the aid of a suspending agent such as acacia, tragacanth, or methylcellulose.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously. adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compounds of Formula I may also be administered in a carrier suitable for topical administration, such carriers include creams. ointments, lotions, pastes, jellies, sprays, aerosols, bath oils, or other pharmaceutical carriers which accomplish direct contact between the compound and the surface of the skin area to be treated. In general pharmaceutical preparations may comprise from about 0.01% to about 10%, and preferably from about 0.1% to about 5% by w/w of the active compound in the suitable carrier.

Additionally, a rectal suppository can be employed to deliver the active compound This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 g.

The term "unit dosage form", as used in the specification. refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on the unique characteristics of the active material and the particular effect to be achieved and the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, drops, ampules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans having an average weight of 70 kg is from about 50 to about 3000 mg of compound in a single dose. More specifically, the single dose is from about 100 mg to 2000 mg of compound. Typically the dosages are given one to four times per day.

The process for making compounds of Formula I is illustrated in Charts A and B. The requirements for protecting groups in the processes of Charts A and B are well recognized by one skilled in the art of organic chemical synthesis and suitable protecting groups are used in the processes of Charts A and B. It is recognized that conditions for introduction and removal of protecting groups should not detrimentally alter any other groups in the molecule.

Examples of suitable nitrogen protecting groups are:
(1) benzyl;
(2) triphenylmethyl (trityl);
(3) trialkylsilyl, such as trimethylsilyl or t-butyldimethyl silyl;
(4) t-butoxycarbonyl (t-BOC or BOC);
(5) benzyloxycarbonyl (Cbz);
(6) trifluoroalkanoyl, such as trifluoroacetyl or trifluoropropionyl; or
(7) diphenyl(methyl)silyl.

Introduction and removal of such nitrogen protecting groups are well known in the art of organic chemistry: See, for example, (1) J. F. W. McOmie, Advances in Organic Chemistry, Vol. 3, pages 191–281 (1963); (2) R. A. Boissonas, Advances in Organic Chemistry, Vol. 3, pages 159–190 (1963); (3) "Protective Groups in Organic Chemistry", J. F. W. McOmie, Ed., Plenum Press, New York. 1973, pg 74, and (4) "Protective Groups in Organic Synthesis", Theodora W. Greene, John Wiley and Sons. New York, 1981.

Under certain circumstances it may be necessary to protect two or more nitrogen atoms with different protecting groups allowing selective removal of one protecting group while leaving the remaining protecting groups in place. For example, the Cbz group can be selectively removed in the presence of the BOC group and vice versa.

The process for making compounds of Formula I is illustrated in Chart A. The starting compound, A-1. can be made by methods known in the art; J. Am. Chem. Soc., 2401–2404 (1973) or by the process illustrated in Chart B. Compound A-1 may be substituted on the lactam ring at the $C_3$ position with $R_1$ where $R_1$ is hydrogen, methoxy or —CO—$NH_2$. Methods for introducing methoxy and —CO—$NH_2$ substituents at $C_3$ of the lactam ring are known in the art; J. Am. Chem. Soc., 2401-2404 (1973).

Compound A-1 reacts with commercially available or known compounds of the formula $HO_2C$—$R_3$—X, where $R_3$ and X are defined above, to prepare compound A-2. The general conditions for conducting this acylation are well known in the art. A preferred method involves reacting compound A-1 with the appropriate carboxylic acid in the presence of dicyclohexylcarbodiimide and 1-hydroxybenzotriazole and a catalytic amount of 4-dimethylaminopyridine. The reaction can be conducted at a temperature of about 0°–30° C. for a time of about 1 to 5 hours. Compound A-2 can be isolated from the reaction mixture by methods known in the art such as crystallization or chromatography.

Compound A-2 reacts with a sulfonating agent to give compounds of Formula I. If necessary, protecting groups well known in the art are placed on sites subject to random sulfonation. A preferred manner of introducing the sulfono group is by reacting dimethylformamide sulfur trioxide with an optionally protected compound A-2 in a suitable solvent. The reaction can be conducted at a temperature of about −20° to 60° C. for a time of about 1 to 5 hours. Preferred reaction temperature and reaction times are about 0° to 25° C. and 1 to 3 hours, respectively. Solvents that can be used include dimethylformamide and methylene chloride. The preferred solvent is dimethylformamide. The sulfonated compound is removed from the reaction mixture by methods known in the art and any protecting groups are removed by known methods to give compounds of Formula I.

Chart B outlines an alternative preparation of compound A-1. The known lactam, B-1; J. Org. Chem., 47:2765–2767 (1982), is silylated on $N_1$ with silylating agents well known in the art. Typically, a trialkylsilyl chloride or an arylalkylsilyl chloride in the presence of an organic base is used. The reaction is conducted at a temperature of about 0° to 25° C. for a period of about 1 to 5 hours in any of several anhydrous solvents. e.g., ethyl acetate, dioxane, tetrahydrofuran, or dimethylformamide, in the presence of either an inorganic base, or a tertiary amine such as trialkylamine or imidazole. A preferred solvent is dimethylformamide.

The silylated azetidinone is then reduced to give the compound B-2. The reduction is conducted in the presence of a metal hydride at a temperature range of 0° C. to room temperature for times of 2 to 5 hours. The preferred method uses lithium borohydride in anhydrous tetrahydrofuran under cold conditions for several hours. The reduced compounds can be purified by methods known in the art.

The protecting group on the $C_3$ positon is removed by hydrogenolysis in the presence of palladium black under hydrogen gas and converted to the amide. B-3, following a variety amide or peptide forming reactions such as those described in Methoden der Organischem Chemie, Vierte Auflage, Band XV/2, E Wunch ed., Georg Thieme Verlag, Stuttgart, p. 1. A preferred acylation process is the use of approximately molar quantities of a desired acid, 1-hydroxy-benzotriazole, and a carbodiimide, such as dicyclohexylcarbodiimide. The reagents are added to the solution of the amine in a solvent, such as tetrahydrofuran- dimethylformamide, or acetonitrile. A temperature of 0°–60° C. is operative, with 20°–35° C. preferred. The time of reaction is variable from 0.5–24 hr being required. although usually 3.4 hr is sufficient A precipitate of dicyclohexylurea is formed during the reaction. This is removed by filtration. The amides are isolated from the filtrate by extractive procedures and chromatography.

After the amidation, the protecting silyl group is removed to give compound A-1. Desilylation is accomplished by reacting compound B-3 with a fluoride ion in the presence of a solvent at a temperature of about −20° to 60° C. for a time of about 1 to 12 hours. Preferred are about 0° to 25° C. and 1 to 5 hours, reaction temperature and times respectively. Solvents that can be used include methylene chloride, methanol, tetrahydrofuran and ethanol. The preferred method of conducting this step is to treat the compound with triethylammonium fluoride in methanol.

Optically active isomers of the disclosed compounds are resolved by methods known in the art; Takeda European patent application 8310461-3. The resolving agents are any of the commercially available and commonly used resolving agents such as optically active camphorsulfonic acid, bis o-toluoyltartaric acid, tartaric acid, and diacetyl tartaric acid. Illustrative examples are given in Organic Synthesis, Coll. Vol. V., p. 932 (1978).

Compounds of this invention are converted into optically active diastereomeric salts by reaction with an optically active acid in a manner standard in the isomer resolution art. The optically active acids include the resolving agents described above. These diastereomeric salts can then be separated by methods known in the art. Preferably the separation of enantiomers is carried out by forming salts of optically active tartaric acid or derivatives thereof and taking advantage of the difference in solubility between the resulting diastereomers Salt formation is carried out prior to acylation of the amino acid moiety at the $C_4$ position of the azetidinone ring. The preferred starting compound for making optically active compounds of Formula I, cis-($\pm$)-1[(2', 4'-dimethoxyphenyl)methyl]-4-(methoxycarbonyl)-3-phenylmethoxycarboxyamido-2-azetidinone, is known; Chem. Pharm. Bull., 32:2646–2659 (1984). The $C_3$ protecting group is removed by hydrogenolysis to the corresponding free amine. An appropriate substituted tartaric acid enantiomer is then added such as (+)-di-p-toluoyl-D-tartaric acid and reaction conditions altered to facilitate precipitation of the appropriate azetidinone diastereomeric salt. The tartaric acid is removed by treating the compound with inorganic base such as sodium bicarbonate to obtain enatiomerically pure amino-azetidinone which is made into compounds of Formula I by the methods described above.

Without further elaboration, it is believed that one skilled in the art can, using the preceding description, practice the present invention. The following detailed examples describe how to prepare the various compounds and are to be construed as merely illustrative, and not limitations of the preceding disclosure. Those skilled in the art will recognize appropriate variations in reactants and reaction conditions and techniques which are equivalent to the described procedures.

EXAMPLE 1

Cis-($\pm$)-1-t-butyldimethylsilyl-3-[[2'-(phenylmethoxy)carbonyl]-amino]4-methoxycarbonyl-2-azetidinone.

The reagent, t-butyldimethylsilylchloride (33.4 g), is added with stirring to a solution of cis-($\pm$)-4-(methoxycarbonyl)-2 -oxo-3[[(phenylmethoxy)carbonyl]amino]-1-azetidine (56.1 g), triethylamine (26.5 g) and 4-dimethylaminopyridine (3.3 g) in anhydrous dimethylformamide (300 ml) at 0° C. After 30 minutes the reaction temperature is warmed to room temperature and stirred for 3 hours. The precipitated solid is filtered and the filtrate is concentrated under reduced pressure. The residue is dissolved in ethyl acetate, washed with water, dried over anhydrous sodium sulfate and concentrated under reduced pressure to give the title compound (71.9 g).

Melting point: 115°–117° C.

EXAMPLE 2

Cis-(±)-1-t-butyldimethylsilyl-4-hydroxymethyl-3-[[2-(phenylmethoxy)carbonyl]amino]-2-azetidinone.

Lithium borohydride (1.47 g) is added to a stirred solution of cis-(±)-1-t-butyldimethylsilyl-3-[[2'-(phenylmethoxy)carbonyl]amino]-4-methoxycarbonyl-2-azetidinone (6.907 g) in anhydrous tetrahydrofuran (50 ml) at 0° C. The reaction mixture is kept at 0° C. for 4 hours and then is quenched by slowly adding acetic acid (16 ml) solution in ethyl acetate (50 ml) and aqueous sodium bicarbonate solution. The organic layer is washed with brine, dried over anhydrous sodium sulfate and concentrated under reduced pressure to give a viscous material. This crude product is passed through a silica gel column eluting with hexane/ethyl acetate (2:1), which affords the title product (5.15 g).

$^1$H-NMR($\delta$, CDCl$_3$) 7.4, 6.05, 5.25, 3.85, 2.45, 0.9, 0.35, 0.25.

EXAMPLE 3

Cis-(±)-1-t-butyldimethylsilyl-4-hydroxymethyl-3-amino-2-azetidinone.

Palladium-black (2.5 g) in ethanol (20 ml) is added to a solution of cis-(±)-1t-butyldimethylsilyl-4-hydroxymethyl-3-[[2'-(phenylmethoxy)carbonyl]amino]-2-azetidinone (5.0 g) in methanol (50 ml) under one atmosphere of hydrogen gas at room temperature. The reaction is complete in 40 minutes Toluene (10 ml) is added to the mixture and stirred for 5 minutes. The catalyst is filtered and washed with methanol. The filtrate is concentrated under reduced pressure to give the title compound (3.16 g).

EXAMPLE 4

Cis-(±)-1(t-butyldimethylsilyl)-3-[2'-(2''-triphenylmethylamino-4''-thiazolyl)-(Z)-2'-(methoxyimino)acetamido]-4-hydroxymethyl-2-azetidinone.

Dicyclohexylcarbodiimide (347 mg) is added to a mixture of cis-(±)-1-t-butyldimethylsilyl-4-hydroxymethyl-3-amino-2-azetidinone (320 mg), 2-(2'-triphenylmethylamino)-2-(methoxyimino) acetic acid (860 mg, 87% purity by weight), 1-hydroxybenzotriazole (227 mg) in methylene chloride (10 ml) at 0° C. After one hour the ice bath is removed and the reaction mixture is kept at ambient temperature overnight. The solid is filtered and washed with methylene chloride (30 ml). Aqueous sodium bicarbonate solution (10 ml) is added to the filtrate, stirred for 20 minutes, dried over anhydrous sodium sulfate and concentrated under reduced pressure. Preparative thin layer chromatography on silica gel developing with 3:1/hexane:ethyl acetate gives the title compound (700 mg). $^1$H-NMR ($\delta$, CDCl$_3$) 7.25, 6.45, 5.4, 3.95, 4.35~3.7, 0.9, 0.35, 0.25.

EXAMPLE 5

Cis-(±)-3-[2'-(2''-triphenylmethylamino-4''-thiazolyl)—(Z)-2'-(methoxyimino)acetamido]-4-hydroxymethyl-2-azetidinone.

A 1M solution of aqueous triethylammonium fluoride in methylene chloride (1.5 ml) is added to a solution of cis-(±)-1-(t-butyldimethylsilyl)-3-[2'-(2''-triphenylmethylamino-4''-thiazolyl)—(Z)-2'-(methoxyimino)acetamido}-4-hydroxymethyl-2-azetidinone (656 mg) in methanol (10 ml) at room temperature. After one hour solid sodium bicarbonate (100 mg) is added to the reaction mixture and the reaction is concentrated under reduced pressure. Ethyl acetate (100 ml) and water (50 ml) are added to the residue, the organic layer is dried over anhydrous sodium sulfate and concentrated under reduced pressure to give the title product (509 mg).

$^1$H-NMR($\delta$, CDCl$_3$) 7.25, 6.65, 6.4, 5.4, 3.95, 4~3.5, 8.73, 8.3, 7.32, 6.8, 5.76. 5.15, 4.75. 3.8, 3.75~3.25.

EXAMPLE 6

Cis-(±)-3-[2'-(2''-triphenylmethylamino-4''-thiazolyl)-(Z)-2'-(methoxyimino)acetamido]-4-L-pyroglutamoyloxymethyl-2-azetidinone.

Dicyclohexylcarbodiimide (445 mg) is added to a heterogeneous mixture of cis-(±)-3-[2'-(2''-triphenylmethylamino-4''-thiazolyl) -(Z)-2'-(methoxyimino)acetamido]-4-hydroxymethyl-2-azetidinone (1.0 g), L-pyroglutamic acid (256 mg), 1-hydroxybenzotriazole (243 mg) and a small amount of 4A molecular sieves in anhydrous tetrahydrofuran (20 ml) at room temperature. After 16 hours, the solid is filtered, washed with methylene chloride (100 ml) and the filtrate is stirred for 30 minutes in the presence of aqueous sodium bicarbonate solution. The organic layer is dried over anhydrous sodium sulfate, concentrated under reduced pressure and is passed through a medium pressure silica gel column eluting with 6:1/ethyl acetate:methanol to give the title compound (876 mg).

$^1$H-NMR($\delta$, CD$_3$OD) 7.3, 6.8, 5.25. 5.0~4.5, 3.9, 2.4~2.1.

EXAMPLE 7

Cis-(±)-3[2'-(2''-amino-4''-thiazolyl)-(Z)-2'-(methoxyimino)acetamido]-4-[L-pyroglutamoyl-oxymethyl]-2-oxo-1-azetidinesulfonic acid monopotassium salt (Compound 7) and cis-(±)-[2-(2'-amino-4'-thiazolyl)-(Z)-2-(methoxyimino)-acetamido]-4-[L-pyroglutamoyl-N-sulfonic acid-oxymethyl]-2-oxo-1-azetidinesulfonic acid dipotassium salt (Compound 2).

A 0.9M solution of sulfur trioxide in dimethylformamide (9 ml) is added to a solution of cis-(±)-3-[2'-(2''-triphenylmethylamino-4'-thiazolyl)-(Z)-2(methoxyimino)acetamido]-4-[L-pyroglutamoyloxymethyl]-2-azetidinone (740 mg) in methylene chloride (5 ml) at room temperature and the reaction mixture is kept at ambient temperature for 45 minutes. Additional dimethylformamide-sulfur trioxide solution (0.5 ml) is added and after 20 minutes aqueous monobasic potassium phosphate (408 mg) in water (10 ml) is added followed by methylene chloride (30 ml) The organic layer is taken, dried over anhydrous sodium sulfate and concentrated under reduced pressure. The residual material is dissolved in 70% formic acid (6 ml) and kept at room temperature for 3 hours. The solid is filtered, washed with 70% formic acid (10 ml) and the filtrate is concentrated under reduced pressure to give 620 mg of material.

The sulfonic acid compound is dissolved in water (40 ml) and an aqueous potassium bicarbonate solution is added adjusting pH to 6.5. The small amount of insoluble material is filtered and the filtrate is lyophilized to give 500 mg of material. This crude product is passed through a column of HP-20 resin eluting with water to give the dipotassium salt (59 mg) and the monopotassium salt (18 mg). An additional 100 mg of the monosulfonate compound is giveed by eluting the column with 20% acetone in water. Monopotassium salt: ¹H NMR (δ, D₂O) 7.02, 5.04 and 5.01, 4.98~4.4, 4.0 and 3.96, 2.65~2.0. Dipotassium salt: ¹H NMR (δ, D₂O) 7.02 and 7.0, 5.62 and 5.54, 4.85-4.35, 4.0 and 3.96, 2.85~2.0.

EXAMPLE 8

Cis-(±)-3-[2'-(2"-triphenylmethylamino-4"-thiazolyl)-(Z)-2'-(methoxyimino)acetamido]-4-L-N-phenylmethoxycarbonylpyroglutamoly-oxmethyl-2-azetidinone.

A mixture of cis-(±)-3-(2"-triphenylmethylamino-4"-thiazolyl)-(Z)-2'-(methoxyimino)acetamido]-4-hydroxymethyl-2-azetidinone (454 mg), L-phenylmethoxycarbonylpyroglutamic acid (230 mg), 1-hydroxybenzotriazole (113 mg), dicyclohexylcarbodiimide (207 mg) and dimethyl aminopyridine (30 mg) in anhydrous tetrahydrofuran (20 ml) is stirred at room temperature for one day. Additional phenylmethoxycarbonylpyroglutamic acid (40 mg) is added and allowed to stand for 10 hours. The solid is filtered, washed with ethyl acetate (200 ml) and the filtrate is stirred in the presence of aqueous sodium bicarbonate solution. The organic layer is taken, dried over sodium sulfate and concentrated under reduced pressure. Preparative thin layer chromatography on silica gel of this crude product developing with ethylacetate/hexane/methanol (4:4:1) affords the title compound (580 mg).

¹H-NMR(δ, CDCl₃) 7.36~0.29, 6.7, 5.9, 5.25, 4.75~4.1, 4.0, 2.7~1.9.

EXAMPLE 9

Cis-(±)-3[2'-(2"-amino-4"-thiazolyl)-(Z)-2'-(methoxyimino) acetamido]-4-[-L-N-phenylmethoxycarbonyl pyroglutamoyl-oxymethyl]-2-oxo-1-azetidinesulfonic acid potassium salt (Compound 3).

The title compound is prepared by a procedure similar to the one described in Example 7, sulfonation of cis-(±)-3-[2'-(2"-triphenylmethylamino-4"-thiazolyl)-(Z)-2'-(methoxyimino)acetamido]-4-[L-N-phenylmethoxycarbonylpyroglutamoyl-oxymethyl]-2-azetidinone followed by detrytilation, potassium salt formation and purification using Hp-20 resin.

¹H-NMR(δ, D₂O) 7.5, 7.0 and 6.98, 5.5~4.3, 3.98 and 3.97, 2.8~2.0.

EXAMPLE 10

Cis-(±)-3-[2'-(2"-triphenylmethylamino-4"-thiazolyl)-(Z)-2'-(methoxyimino)acetamido]-4-N-acetylglycinoyl)-oxymethyl-2-azetidinone.

A mixture of cis-(±)-3-[2'-(2"-triphenylmethylamino-4"-thiazolyl)-(Z)-2'-(methoxyimino)acetamido]-4-hydroxymethyl-2-azetidinone (542 mg), 1-hydroxybenzotriazole (1.04 mmole), N-acetylglycine (180 mg), dicyclohexylcarbodiimide (340 mg) and small amount of 4 Å molecular sieve in dimethylformamide (5 ml) is stirred at room temperature for 2 days. The solid material is filtered, washed with ethyl acetate (100 ml) and the filtrate is stirred in the presence of aqueous sodium bicarbonate solution (300 mg of sodium bicarbonate in 25 ml of water) for 20 minutes. The organic layer is taken, dried over sodium sulfate and concentrated under reduced pressure. The residue is passed through a medium pressure silica gel column eluting with hexane/ethyl acetate (1:1) followed by hexane/ethyl acetate (1:2) and then ethyl acetate to give the title compound (360 mg).

¹H-NMR(δ, CDCl₃) 7.9, 7.28, 7.0, 6 63, 5.3. 3.94, 3.75, 4.4~4.0, 1.92.

EXAMPLE 11

Cis-(±)-3-[2'-(2"-amino-4"-thiazolyl)-(Z)-2'-(methoxyimino) acetamido]4-[N-acetylglycinoyl-oxymethyl]-2-oxo-1-azetidine sulfonic acid potassium salt (Compound 5).

A 0.95M solution of sulfur trioxide in dimethylformamide (0.5 ml) is added to a solution of cis-(±)-3-[2-(2"-triphenylmethylamino-4"-thiazolyl)-(Z)-2'-(methoxyimino)acetamido]-4-[N-acetylglycinoyl-oxymethyl]-2-azetidinone (300 mg) in methylene chloride (3 ml) at 0° C. and it is kept at 0° C. for 20 minutes. An additional 0.25 ml of dimethylformamide,sulfur trioxide solution is added and stirred at 0° C. for 20 minutes The reaction is quenched by adding aqueous potassium phosphate monobasic (150 mg in 5 ml water) followed by tetra-N-butylammonium hydrogen sulfate (340 mg). The sulfonated product is extracted with methylene chloride (50 ml), dried over sodium sulfate and concentrated under reduced pressure. The material giveed is dissolved in 70% formic acid (10 ml) and after 4 hours detrytilation is complete. The solid is filtered, washed with 70% formic acid (10 ml) and the filtrate is concentrated under reduced pressure. Potassium salt formation is made by passing this tetra-n-butylammonium salt through Dowex-K+resin and purification by HP-20 resin column chromatograph to give the title compound (200 mg). ¹H-NMR(δ, CD₃OD) 6.84, 5.35, 4.47. 3.96, 3.93, 1.98.

EXAMPLE 12

Cis-(±)-3-[2'-(2"-amino-4"-thiazolyl)-(Z)-2'-(methoxyimino)acetamido]4-N-phenylmethoxycarbonyl glycinoyl-oxymethyl-2-oxo-1-azetidinesulfonic acid Potassium salt (Compound 4).

The title compound is produced by following the procedures given in Examples 10 and 11 and substituting N-phenylmethoxycarbonyl glycine methyl ester for N-acetylglycine. ¹H-NMR (δ, CD₃OD) 7.3, 6.85, 5.4, 5.1, 4.8~4.3, 2.95.

EXAMPLE 13

Cis-(±)-3-[2'-(2"-amino-4"-thiazolyl)-(Z)-2'-(methoxyimino)acetamido]-4-[N-formylglycinoyl-oxymethyl]-2-oxo-1-azetidine sulfonic acid potassium salt (Compound 6)

The title compound is produced by following the procedures given in Examples 10 and 11 and substituting N-formylglycine for N-acetyl glycine.

¹H-NMR(δ, CD₃OD) 8.1, 6.85, 5.35, 4.45. 4.05, 3.95, 4.6~4.4.

EXAMPLE 14

Cis-(±)-1-(t-butyldimethylsilyl)-3-[2'-[(2"-t-butoxycarbonylamino)-4"-thiazolyl]-[2'-(1'''-t-butoxycarbonylmethoxy)imino]]-acetamido-4-hydroxymethyl-2-azetidinone.

Dicyclohexylcarbodiimide (3.86 g) is added to a stirred mixture of cis-(±)-1-t-butyldimethylsilyl-4-hydroxymethyl-3-amino-2-azetidinone (3.6 g), 2-(2-t-butoxycarbonylaminothiazol-4-yl)-(Z)-2-(butoxycarbonyl)(methoxyimino)acetic acid (6.9 g) and 1-hydroxybenzotriazole (2.11 g) in methylene chloride (40 ml) in an ice bath. The ice bath is removed after 2 hours and the reaction mixture is stirred overnight at room temperature. The precipitated solid is filtered, washed with methylene chloride (60 ml) and the filtrate is stirred with aqueous sodium bicarbonate (1.5 g sodium bicarbonate in 35 ml water) for 20 minutes at room temperature. The organic layer is taken, dried over sodium sulfate and concentrated under reduced pressure. Treatment of the residual material with ether gives the title compound (4.5 g). The mother liquor is concentrated and passed through the medium pressure silica gel column eluting with 3:1/hexane:ethyl acetate to give additional title compound (2.2 g). $^1$H-NMR($\delta$, CDCl$_3$) 8.2, 8.0, $\delta$ 7 28, 5.5, 4.66, 4.64, 4.0~3.7, 1.6, 1.49, 1.54, 0.96, 0.24, 0.22.

EXAMPLE 15

Cis-($\pm$)-3-[2'-[(2''-t-butoxycarbonylamino)-4''-thiazolyl]2'-[(1'''-t-butoxycarbonylmethoxy)imino]-acetamido-4-hydroxymethyl]-2-azetidinone.

Triethylammonium fluoride in methylene chloride (12.7 mmole, prepared by mixing triethylamine and 48% hydrofluoric acid in methylene chloride in an ice bath) is added at room temperature to a stirred solution of cis-($\pm$)-1-(t-butyldimethylsilyl)-3-[2'-[(2''-t-butoxycarbonyl amino)-4''-thiazolyl]-(Z)-[2'-(1'''-t-butoxycarbonylmethoxy)imino]] acetamido-4-hydroxymethyl azetidinone (6.5 g) in methanol (60 ml) and the solution is allowed to stand for 30 minutes. Sodium bicarbonate solid (4.2 g) is added to the reaction mixture, the methanol is evaporated under the reduced pressure and methylene chloride (150 ml) and water are added (30 ml). The organic layer is taken, dried over sodium sulfate, concentrated under reduced pressure, washed with diethyl ether and dried to give the title compound (4.9 g).

Melting point: 195° C. (decomp.).

EXAMPLE 16

Cis-($\pm$)-3-[2'-[(2''-t-butoxycarbonylamino) -4''-thiazolyl]-(Z)-2-[(1'''-t-butoxycarbonylmethoxy)-imino]]-acetamido-4-N-formylglycinoyl-oxymethyl]-2-azetidinone.

Dicyclohexylcarbodiimide (3.25 g) is added to a stirred mixture of cis-($\pm$)-3-[2'-[(2''-t-butoxycarbonylamino)-4''-thiazolyl]-(Z)-2'-[(1'''-t-butoxycarbonylmethoxy)imino]acetamido-4-hydroxymethyl]-azetidinone (4.5 g), 1 hydroxybenzotriazole 1.216 g), dimethylaminopyridine (122 mg), N-formylglycine (1.62 g) and some 4 Å molecular sieves in methylene chloride (60 ml) and dimethylformamide (6 ml) at room temperature After 2 hours, the precipitated solid is filtered off, washed with methylene chloride (50 ml) and the filtrate is stirred with aqueous sodium bicarbonate (1.89 g sodium bicarbonate in 40 ml water) at room temperature for 15 minutes. The organic layer is taken, dried over sodium sulfate and concentrated under reduced pressure. The residue is passed through the medium pressure silica gel column eluting with 3:1 hexane/ethylacetate followed by ethyl acetate to give the title compound (3.6 g). Melting point: 108°–110° C.

EXAMPLE 17

Cis-($\pm$)-[2'-(2''-amino-4''-thiazolyl)-(Z)-2'-(1''-carboxymethoxy)imino]acetamido-4-[N-formylglycinoyloxymethyl]-2-oxo-1-azetidinesulfonic acid monopotassium salt (Compound 7) and cis-$\pm$-3-[2'-(2''-amino-4''-thiazolyl)-(Z)-2'-(1'''-carboxymethoxy)imino]acetamido-4-[N-formylsulfonic acid glycinoyl-oxymethyl]-2-oxo-1-azetidinesulfonic acid dipotassium salt (Compound 8)

a dimethylformamide-sulfur trioxide solution (2.85 ml of 0.904 M solution) is added t a solution of cis-($\pm$)-3-[2'-[2''-t-butoxycarbonylamino)- 4''-thiazolyl]-(Z)-2'-[(1''''-t-butoxycarbonylmethoxy)-imino]]acetamido-4-N-formylglycinoyl -oxymethyl]-2-azetidinone (1.5 g) in dimethylformamide (5 ml) at 0° C. and stirred for one hour. The ice bath is removed and the solution is kept at ambient temperature for an hour. An additional 1 ml of dimethylformamide-sulfur trioxide complex solution is added. After 45 minutes the reaction is quenched by adding aqueous monobasic potassium Phosphate solution (690 mg monobasic potassium phosphate in 40 ml water) and methylene chloride (50 ml) followed by tetra-N-butylammonium hydrogen sulfate (1.74 g). The organic layer is taken, dried over sodium sulfate and con. centrated under reduced pressure. The residue is dissolved in methylene chloride (10 ml), cooled to 0° C. and trifluoroacetic acid (15 ml) is added with stirring. The ice bath is removed after 2 minutes and the reaction mixture is kept at ambient temperature for 30 minutes. The reaction mixture is concentrated under reduced pressure, washed with hexane (50 ml$\times$5) to remove the residual trifluoroacetic acid and the residual material was again concentrated under reduced pressure. The residue is dissolved in methanol (10 ml) and passed through Dowex-K$^+$ followed by HP-20 resin to give the monopotassium salt (275 mg) and the dipotassium salt (192 mg). Monopotassium salt: $^1$H-NMR($\delta$, D$_2$O, Me$_2$SiCD$_2$CD$_2$COO-NA$^+$as a reference) 8.14, 7 0, 5.2, 4.7~4.53, 4.44, 4.08. Dipotassium salt: $^1$H-NMR($\delta$, D$_2$O, Me$_3$SiCD$_2$CD$_2$COO-Na$^+$as a reference) 8.87, 7.0, 5.54, 4.7~4.5, 4.55, 4.35.

EXAMPLE 18

Cis-(+)-3-[[2'(2''-amino-4''-thiazolyl)-(Z)-2'-(1''-carboxymethoxy)imino]acetamido]-4-[N-formylglycinoyl-oxymethyl]-2-oxo-azetidinesulfonic acid potassium salt (Compound 12).

The optically active title compound is obtained by resolving the enantiomers of cis-($\pm$)-3-phenylmethoxycarboxamido-4-methoxycarbonyl 1(2,4-dimethoxybenzyl)-2-azetidinone. Chem. Pharm. Bull. 32:2–646.2659 (1984). To this racemic mixture (207.3 g) in tetrahydrofuran (500 ml) at room temperature is added palladium black (78.5 g). The hydrogenolysis reaction is carried out under one atmosphere of hydrogen gas. Toluene (100 ml) is added to the reaction mixture and stirred for 15 minutes. The catalyst is removed by filtration and washed several times with tetrahydrofuran. The solvent is evaporated to yield cis-($\pm$)-1-(2'-4'-dimethoxybenzyl)-4-methoxycarbonyl-3-amino-2azetidinone.

The above amino azetidinone is dissolved in acetonitrile (3000 ml) and (+)-di-p-toluoyl-D-tartaric acid (200 g) is added with stirring. The solution is warmed to dissolution and allowed to cool to room temperature. The solid precipitate is then collected by filtration and washed with ice-cold acetonitrile. The solid is recrystallized from acetonitrile to give the tartrate salt of cis-(+)-1-(2',4'-dimethoxybenzyl)-4-methoxycarbonyl-3-amino-2-azetidinone.

The above salt is then dissolved in tetrahydrofuran (1000 ml) and water (400 ml) at 0° C. Sodium bicarbonate (34.9 g) and benzyl chloroformate (26.0 ml) are added with stirring. After one hour at 0° C., the reaction mixture is warmed to room temperature and stirred for 30 min. The reaction mixture is then concentrated under reduced pressure and the aqueous residue is diluted with ethyl acetate (3000 ml) and water (1000 ml). The organic layer is taken and the aqueous layer is rewashed with ethyl acetate (500 ml). The organic layers are combined and washed successively with 2% aqueous sodium bicarbonate, 1N HCl, brine, and 2% aqueous sodium bicarbonate (500 ml each). The organic layer is then dried over sodium sulfate and concentrated under reduced pressure. The resulting material is triturated with ether to give the desired enantiomer, cis-(+)-3-phenylmethoxycarboxamido-4-methoxycarbonyl-1-(2,4-dimethoxybenzyl)-2-azetidinone.

The above enantiomer is treated with ceric ammonium nitrate at 0° C. in acetonitile to yield cis-(+)-3-phenylmethoxycarboxamido-4methoxycarbonyl2-azetidinone. The enantiomer is then reacted under the identical conditions described for Examples 1.5 to yield cis-(+)-3-[2'-(2"-triphenylmethylamino-4"-thiazolyl)-(Z)-2'-(methoxyimino)acetamido-4 -hydroxymethyl-2-azetidinone which is used to produce the title compound following the steps described for Examples 6 and 7.

$^1$H-NMR($\delta$, D$_2$O, ME$_3$S:CD$_2$CD$_2$CO$_2$-Na$^+$as a reference) 8.5, 7.0, 5.5, 4.6, 4.08.

EXAMPLE 19

Cis-(±)-3-[2'-[2"-amino-4"-thiazolyl)-(Z)-2'-(1'''-carboxymethoxy)imino)]-acetamido-4-[L-N-formylalanoyloxymethyl]-2-oxo-1-azetidinesulfonic acid potassium salt (Compound 9)

The title compound is made by a procedure similar to that described in Examples 16 and 17 and substituting L-N-formylalanine for N-formylglycine.

$^1$H-NMR($\delta$, D$_2$O. ME$_3$SiCD$_2$CD$_2$CO$_2$-Na as a reference) 8.2, 5.52, 4.65 and 4.58, 5~4.4, 1.39.

EXAMPLE 20

Cis(±)-3-[2'(2"-amino-4"-thiazolyl)-(Z)-2'-(1'''-carboxymethoxy)imino)]acetamido]-4-[D-N-formylalanoyloxymethyl]-2-oxo-1-azetidinesulfonic acid (Compound 10).

The title compound is made by a procedure similar to that described in Examples 16 and 17 and substituting D-N-formylalanine for N-formylglycine.

$^1$H-NMR($\delta$, D$_2$O, ME$_3$SiCD$_2$CD$_2$CO$_2$-Na as a reference) 8.1, 5.52, 4.7~4.2.

EXAMPLE 21

Cis-(±)-3-[[2'-(2"-amino-4"-thiazolyl)-(Z)-2'-(1'''-carboxymethoxy)imino]acetamido]-4-[N-glycinoyl oxymethyl]-2-oxo-1-azetidinesulfonic acid (Compound 11).

The titled compound is made by a procedure similar to that described in Examples 16 and 17 and substituting N-t-butoxycarbonylglycine for N-formylglycine. $^1$H-NMR($\delta$, D$_2$O, ME$_3$SiCD$_2$CD$_2$CO$_2$-Na as a reference) $\delta$7.0, 5.25, 4.97~4.62, 3.95.

TABLE 1
ANTIMICROBIAL IN VITRO TESTING
Minimum Inhibitory Concentration -MCG per ML-

| Organism Name | Culture No. | Compound 7[1] | Compound 11[2] |
|---|---|---|---|
| Staphylococcus aureus | 6675 | >128 | >128 |
| Staphylococcus aureus | 3665 | >128 | >128 |
| Staphylococcus aureus | 6685 | >128 | >128 |
| Streptococcus faecalis | 694 | >128 | >128 |
| Streptococcus pneumoniae | 41 | 64 | 128 |
| Streptococcus pyogenes | 152 | 16 | 16 |
| Citrobacter freundii | 3507 | 0.125 | 0.25 |
| Enterobacter cloacae | 9381 | 64 | 64 |
| Enterobacter cloacae | 9382 | 0.125 | 0.25 |
| Escherichia coli | 311 | 0.06 | 0.125 |
| Escherichia coli | 9451 | 0.125 | — |
| Escherichia coli | 9379 | 0.125 | 0.25 |
| Escherichia coli | 9380 | 0.25 | 0.25 |
| Klebsiella oxytoca | 9383 | 0.5 | 1 |
| Klebsiella oxytoca | 9384 | 0.06 | 0.125 |
| Klebsiella pneumoniae | 58 | 0.06 | 0.125 |
| Proteus vulgaris | 9679 | <0.03 | 0.125 |
| Serratia marcescens | 6888 | 0.25 | 0.5 |
| Pseudomonas aeruginosa | 9191 | 4 | 8 |
| Pseudomonas aeruginosa | 6432 | 8 | 64 |
| Pseudomonas aeruginosa | 6676 | 4 | 8 |
| Pseudomonas aeruginosa | 30133 | 8 | 16 |

[1]Compound 7 is cis-(±)-3-[2'(2"-amino-4"-thiazolyl)-(Z)-2'-(1'"-carboxymethoxy)imino]acetamido]-4-[N—formylglycinoyl-oxymethyl]-2-oxo-azetidinesulfonic acid potassium salt.
[2]Compound 11 is cis-(±)-3-[[2'-(2"-amino-4"-thiazolyl)-(Z)-2'-(1'"-carboxymethoxy)imino]acetamido]-4-[N—glycinoyl-oxymethyl]-2-oxo-1-azetidine sulfonic acid.

FORMULAS

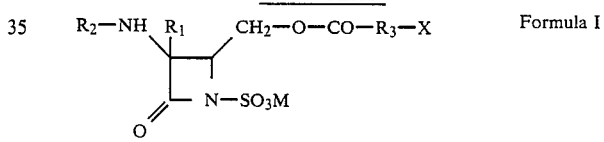

Formula I

Formula II

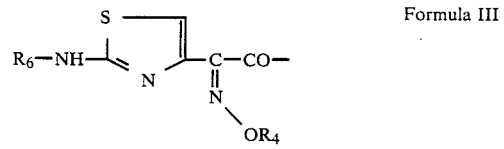

Formula III

STRUCTURE CHARTS

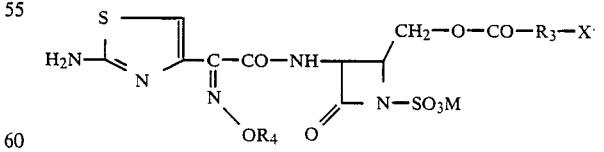

| Compound No. | R$_4$ | R$_3$—X | M |
|---|---|---|---|
| 1 | —CH$_3$ | 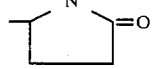 | K |

STRUCTURE CHARTS -continued

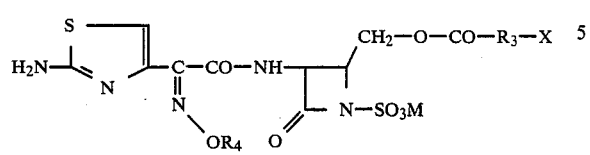

| Compound No. | R₄ | R₃—X | M |
|---|---|---|---|
| 2 | —CH₃ | 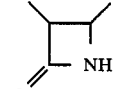 SO₃K | K |
| 3 | —CH₃ | 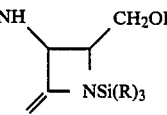 CO₂CH₂C₆H₅ | K |
| 4 | —CH₃ | —CH₂NHCO₂CH₂C₆H₅ | K |
| 5 | —CH₃ | —CH₂NHCOCH₃ | K |
| 6 | —CH₃ | —CH₂NHCHO | K |
| 7 | —CH₂CO₂H | —CH₂NHCHO | K |
| 8 | —CH₂CO₂H | —CH₂NH(SO₃K)CHO | K |
| 9 | —CH₂CO₂H | —CH(CH₃)NHCHO | K |
| 10 | —CH₂CO₂H | (D) —CH(CH₃)NHCO | K |
| 11 | —CH₂CO₂H | —CH₂NH₂ | K |
| 12 | —CH₂CO₂H | (D) —CH₂NACOH | K |
| 13 | —C(CH₃)₂CO₂H | —CH₂NHCOH | K |
| 14 | —C(CH₃)₂CO₂H | (D) —CH(CH₃)NHCHO | K |
| 15 | —C(CH₃)₂CO₂H | (L) —CH(CH₃)NHCHO | K |

CHART A

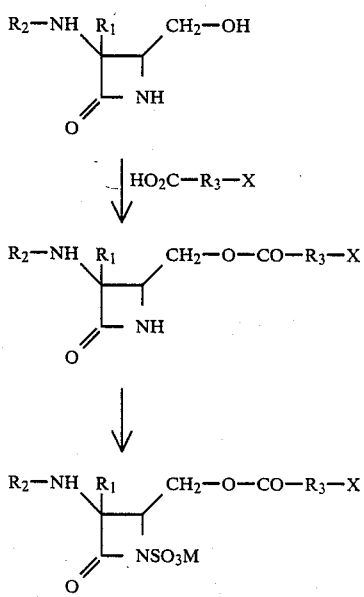

CHART B

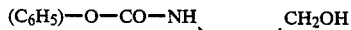
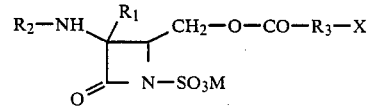

I claim:
1. A compound of the formula,

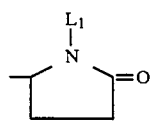

and pharmaceutically acceptable salts thereof; wherein R₁ is hydrogen, —OCH₃, —NH—CHO; wherein R₂ is an acyl group derived from a carboxylic acid; wherein R₃ is selected from the group consisting of —CH—, —CH₂CH₂—, —CH₂CH₂CH₂—, and —CH₂CH₂CH₂CH₂—, and when X is NL₂L3 then —CH₂CH₂—, —CH₂CH₂CH₂—, and —CH₂CH₂CH₂CH₂— are optionally substituted with one substituted selected from the group consisting of (C₁-C₄) alkyl, (C₁-C₄)carboxyalkyl, or (C₁-C₄) alkylthio;

wherein X is —NL₂L3 or is pyrrole, except when R₃ is —CH₂CH₂CH₂CH₂—, of the formula

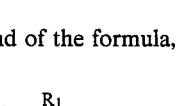

wherein L₁ is
a. hydrogen
b. —CO—O—CH₂—(C₆—H₅), or
c. SO₃H;
wherein L₂ is a. hydrogen, or
b. SO₃H; and L₃ is
a. hydrogen
b. —CO—(C₁-C₄)alkyl,
c. —CH=NH,
d. —C(NH₂)=NH,
e. —CO—O—CH₂—(C₆H₅),
f. —COH, or
g. —SO₃H with the proviso that if one of L₂ or L₃ is —SO₃H then the other is hydrogen.

2. A compound of claim 1 wherein R₂ is an oximinoacyl moiety of the formula;

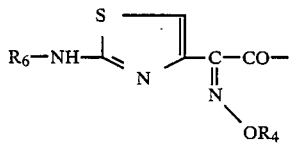

wherein R₄ is —CH₃, —CH₂—CO₂—R₅, or —C(CH₃)₂—CO₂—R₅,
wherein R₅ is
a. hydrogen,
b. (C₁-C₄) alkyl.
c. —CH(C₆H₅)₂,
d. —CH₂(C₆H₅), or
e. a pharmaceutically acceptable cation,
wherein R₆ is
a hydrogen,
b. —CO—O—C(CH₃)₃,
c. —CO—O—CH₂—(C₆H₅), or
d. —C(C₆H₅)₃.

3. A compound of claim 2; wherein R₄ is —CH₃.

4. A compound according to claim 3, selected from the group consisting of 3-[2′-(2″-amino-4″-thiazolyl)-(Z)-2′-(methoxyimino)acetamido]-4-[N-phenylmethoxycarbonylglycinoyl-oxymethyl]-2-oxo-1-azetidinesulfonic acid potassium salt; 3-[2′-(2″-amino-4′-thiazolyl)-(Z)-(methoxyimino)acetamido]-4-[N-acetylglycinoyl oxymethyl]-2-oxo-1azetidinesulfonic acid potassium salt; 3-[2′-(2″-amino-4″-thiazolyl)-(Z)-2′-(methoxyimino)acetamido]-4-[L-pyroglutamoyloxymethyl]-2-oxo-1-azetidinesulfonic acid potassium salt; 3-[2-(2′-amino-4″-thiazolyl)-(Z)-2′-(methoxyimino)acetamido]-4″-thiazolyl)-(Z)-2′-(methoxyimino)acetamido]-4-[L-pyroglutamoyl-N-sulfonic acid-oxymethyl]-2-oxo-1-azetidinesulfonic acid dipotassium salt; 3-[2′-(2″-amino-4″-thiazolyl)-(Z)-2′-(methoxyimino)acetamido]-4-[L-pyroglutamoyl-N-phenylmethoxycarbonyloxymethyl]-2-oxo-1-azetidinesulfonic acid potassium salt; 3-[2′-(2″-triphenylmethylamino-4″-thiazolyl)-(Z)-2′-(methoxyimino)acetamido]-4-[L-N-phenylmethoxycarbonylpyroglutamoyl-oxymethyl]-2-azetidinone; 3-[2′-(2″-triphenylmethylamino-4″-thiazolyl)-(Z)2′-(methoxyimino)acetamido]-4-[N-acetylglycinoyl-oxymethyl]-2-azetidinone; and 3-[2′-(2″-triphenylmethylamino-4″-thiazolyl)-(Z)-2′-(methoxyimino)acetamido]-4-[L-pyroglutamoyl-oxymethyl]-2-azetidinone.

5. A compound of claim 3; wherein R₄ is —CH₂CO₂R₅.

6. A compound according to claim 5 selected from the group consisting of 3-[[2′-(2″-amino-4-thiazolyl)-(Z)-2′-(1‴-carboxymethoxy)-imino]acetamido]-4-[N-formylglycinoyl-oxymethyl]-2-oxo-1-azetidine-sulfonic acid potassium salt, 3-[[2′-(2″-amino-4″-thiazolyl)-(Z)-2′(1‴-carboxymethoxy)imino]acetamido]-4-[N-glycinoyl-oxymethyl]-2-oxo-1-azetidinesulfonic acid potassium salt; 3-[[2′-(2″-amino-4″-thiazolyl)-(Z)-2′-(1‴-carboxymethoxy)imino]acetamido]-4-[N-formylsulfo-glycinoyl-oxymethyl]-2-oxo-1-azetidinesulfonic acid dipotassium salt; 3-[[2′-(2″-amino-4″-thiazolyl)-(Z)-2′-(1‴-carboxymethoxy)imino]acetamido]4-[L-N-formylalanoyl-oxymethyl]-2-oxo-1-azetidinesulfonic acid potassium salt; and 3-[[2′-(2″-amino-4″-thiazolyl)-(Z)-2′-(1‴-carboxymethoxy)imino]acetamido]4[D-N-formylalanoyl-oxymethyl]-2-oxo-1-azetidinesulfonic acid potassium salt.

7. A compound according to claim 7, selected from the group consisting of 3-[2′-(2″-amino)-4″-thiazolyl]-(Z)-2′-[(1‴-t-butoxycarbonylmethoxy)imino]acetamido]4-[N-formylaglycinoyl-oxymethyl-2-oxo-1-azetidinesulfonic acid; 3-[[2′-(2″-amino)-4″-thiazolyl]-(Z)-2′-[(1‴-t-butoxycarbonylmethoxy)imino]acetamido]-4-[D-N-formylalanoyloxymethyl]-2-oxo-1-azetidinesulfonic acid; and 3-[[2′-(2″-amino)-4″-thiazolyl]-(Z)-2-[(1‴-t-butoxycarbonylmethoxy)imino]acetamido-4-[L-N-formylalanoyl-oxymethyl]-2-oxo-1-azetidinesulfonic acid.

* * * * *